US00PP21217P2

(12) United States Plant Patent
Henny et al.

(10) Patent No.: US PP21,217 P2
(45) Date of Patent: Aug. 17, 2010

(54) ***EPIPREMNUM* PLANT NAMED 'UFM12'**

(50) Latin Name: *Epipremnum aureum*
Varietal Denomination: UFM12

(75) Inventors: Richard Henny, Tavares, FL (US); Jianjun Chen, Apopka, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 12/316,132

(22) Filed: Dec. 9, 2008

(51) Int. Cl.
*A01H 5/00* (2006.01)

(52) U.S. Cl. ..... Plt./373

(58) Field of Classification Search ..... Plt./373
See application file for complete search history.

*Primary Examiner*—Annette H Para

(57) ABSTRACT

A new *Epipremnum* plant particularly distinguished by having small variegated leaves with three different colors, irregularly undulated rather than smooth leaf surfaces, and compact and dense growth habit, is disclosed.

2 Drawing Sheets

ACKNOWLEDGEMENT OF FEDERAL RESEARCH SUPPORT

This invention was made with government support under FLA-APO-04158 awarded by the Cooperative State Research, Education, and Extension Service, USDA. The government has certain rights in the invention.

Genus and species: *Epipremnum aureum.*

Variety denomination: 'UFM12'.

BACKGROUND OF THE NEW PLANT

The invention relates to a new and distinct variety of *Epipremnum* plant, botanically known as *Epipremnum aureum* and hereinafter referred to by the variety denomination of 'UFM12'. 'UFM12' originated by exposing cuttings of *Epipremnum aureum* cultivar 'Marble Queen', not patented, to gamma-ray radiation from a Colbalt 60 source at the Florida Accelerator Services and Technology Division of Plant Industry; Florida Department of Agriculture and Consumer Services in Gainesville, Fla. After treatment, the cuttings were grown in a controlled environment in Apopka, Fla. The inventors selected the new *Epipremnum* approximately 1 year later as a single branch mutation within the population of treated plants.

Asexual reproduction of the new cultivar by tip cuttings in a controlled environment in Apopka, Fla. has shown that the unique features of this new *Epipremnum* are stable and reproduced true to type in successive generations of asexual reproduction.

Plant Breeder's Rights for this cultivar have not been applied for. 'UFM12' has not been made publicly available more than one year prior to the filing of this application.

SUMMARY OF THE INVENTION

The cultivar 'UFM12' has not been observed under all possible environmental conditions. The phenotype may vary somewhat with variations in environment such as temperature and light intensity, without, however, any variance in genotype.

The following traits have been repeatedly observed and are determined to be the unique characteristics of 'UFM12'. These characteristics in combination distinguish 'UFM12' as a new and distinct cultivar of *Epipremnum:*

1. Small variegated leaves with three different colors.
2. Leaf surfaces tend to be irregularly undulated rather than smooth.
3. Compact and dense growth habit.

DESCRIPTION OF THE PHOTOGRAPHS

This new *Epipremnum* plant is illustrated by the accompanying photographs which show the plant's overall appearance. These photographs show the colors as true as it is reasonably possible to obtain in colored reproductions of this type. Colors in the photographs may differ slightly from the color values cited in the detailed botanical description which accurately describe the colors of the new *Epipremnum.*

DESCRIPTION OF THE NEW CULTIVAR

Figure 1:
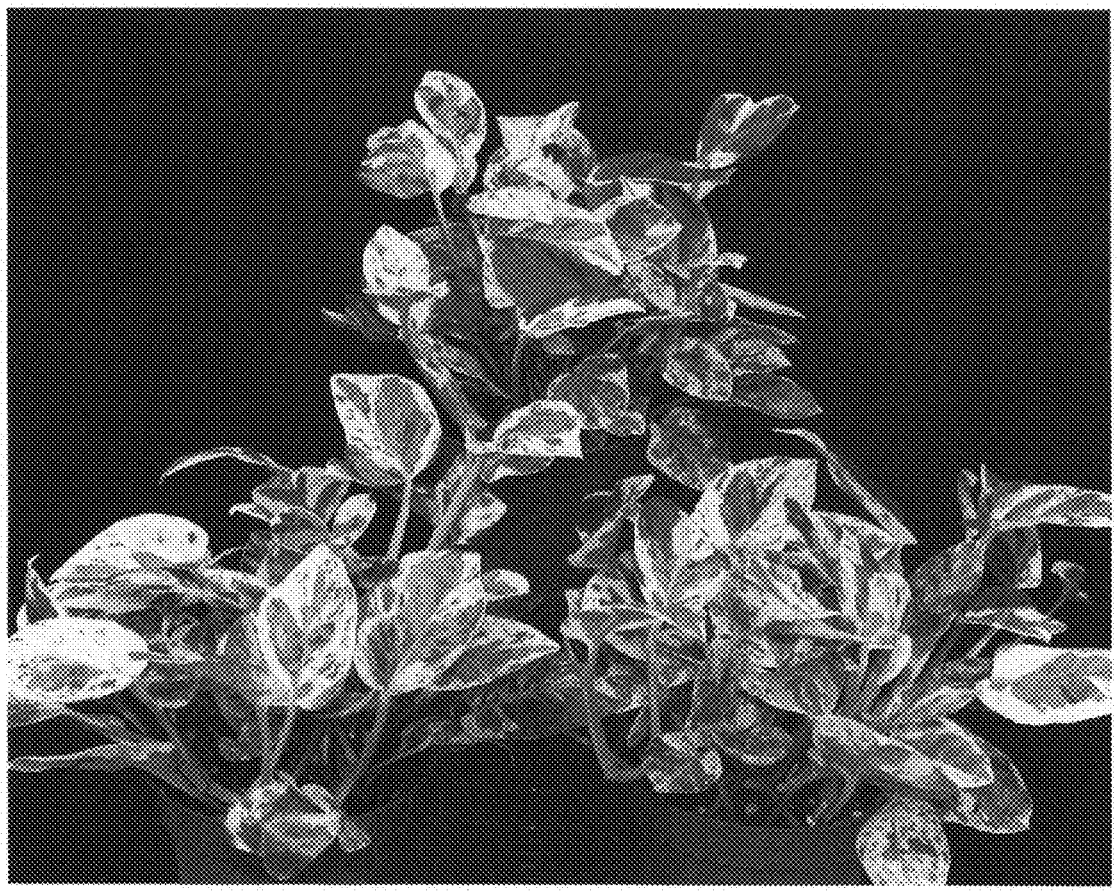
FIG. 1 shows a side perspective view of 3 typical plants of 'UFM12' grown in a 12 cm diameter containers.
Figure 2:
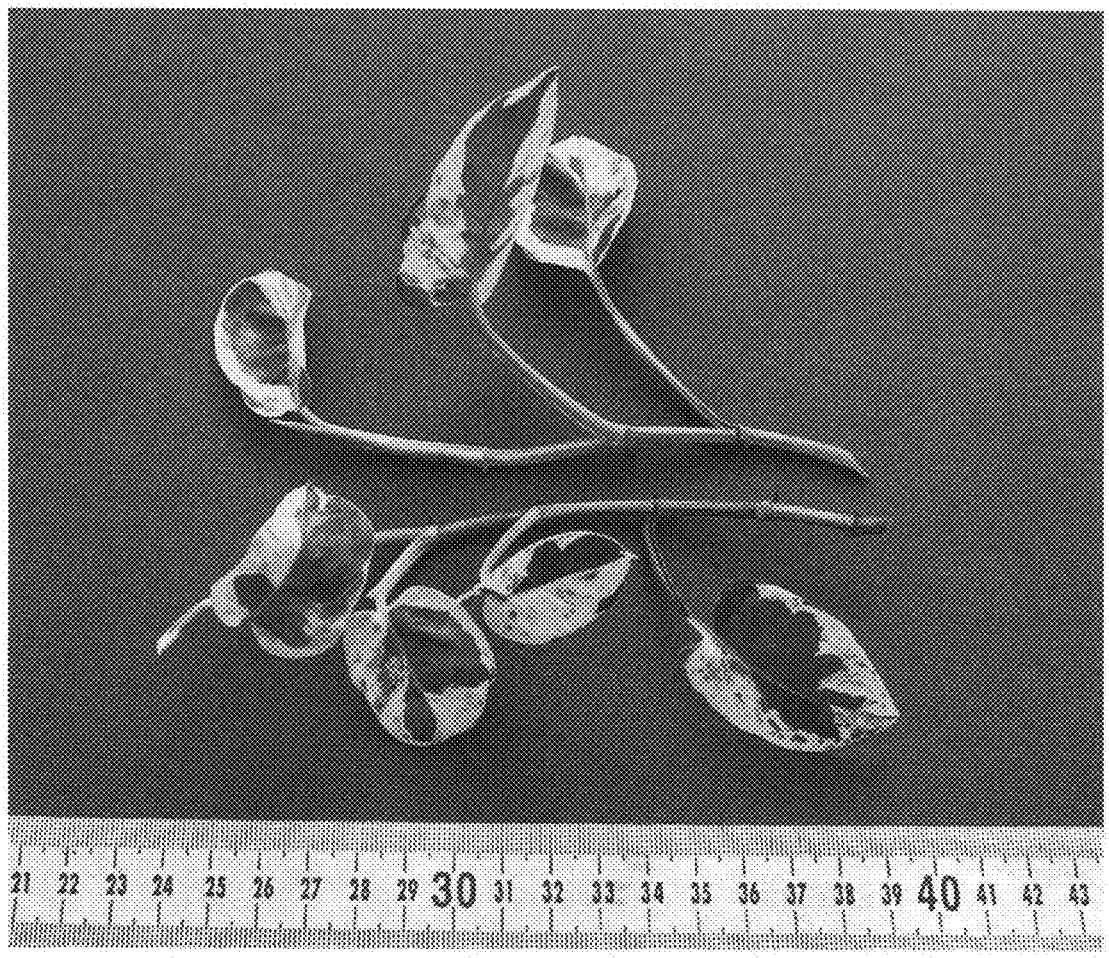
FIG. 2 shows a close-up view of typical vines and typical foliar variegation of 'UFM12'.

The following detailed description sets forth the distinctive characteristics of 'UFM12' with color terminology in accordance with The Royal Horticultural Society Colour Chart, 2001 Edition, except where general terms of ordinary significance are used. The aforementioned photographs and following observations and measurements describe plants grown in containers in Apopka, Fla. during the spring and early summer in a glass-covered greenhouse. Plants were grown using practices and under conditions that approximate those generally used in commercial *Epipremnum* production. During the production of the plants, day temperature ranged from about 29° C. to 35° C., night temperature ranged from a bout 18° C. to 26° C. and light levels were about 2,500 foot-candles.

Plants were grown from single stem cuttings and were about 4 months old when the photographs and the detailed description were taken.

DETAILED BOTANICAL DESCRIPTION

Classification:

*Botanical.—Epipremnum aureum.*

*Common name.*—Pothos.

Parentage: *Epipremnum aureum* cultivar 'Marble Queen' (not patented).

Propagation:

*Type.*—By tip cuttings.

*Time to initiate roots, summer.*—About 21–28 days at 25° C. to 35° C.

*Time to initiate roots, winter.*—About 28–35 days at 15° C. to 30° C.

*Time to produce a rooted young plant, summer.*—About 40 days at 25° C. to 35° C.

*Time to produce a rooted young plant, winter.*—About 50 days at 15° C. to 30° C.

*Root description.*—Medium thick, fleshy; typical of species.

Plant description:

*Plant/growth habit.*—Low growing, trailing, cascading. Plants are full, compact and have dense foliage.

*Plant height, from soil level to top of leaf plane.*—10–12 cm.

*Crop time.*—From sticking 10 unrooted cuttings per container, about 14 to 16 weeks are required to produce finished plants in 10 cm containers.

*Plant diameter or spread.*—About 18 to 22 cm.

*Stem description.*—Length: About 20 to 25 cm. Diameter: About 3 to 4 mm. Internode length: About 3 to 5 cm. Texture: smooth Branching: stems do not tend to branch. Color, immature: 191B with faint stripes of 191C. Color, mature: alternating bands of grayed-green (191A) and grayed-green (191B) that yield a striped appearance.

Foliage description:

*Leaves.*—Arrangement: alternate. Length: About 5 to 7 cm. Width: About 3.5 to 5 cm. Shape: Ovate. Apex: Acuminate. Base: Cordate. Aspect: Mostly undulate and horizontal. Margin: Mostly undulate. Texture, upper and lower surfaces: Undulate. Color immature expanding leaves upper surface: variable; areas of 137A, 191A, and 155A/B. Lower surface: the areas of 137A on upper surface appear lighter as 137C on lower surface, while 191A and 155A/B appear as the same. Color mature leaves upper surface: variable; areas of 137A, 191A, and 155A/B. Lower surface: the areas of 137A on upper surface appear lighter as 137C on lower surface, while 191A and 155A/B appear as the same.

*Petiole.*—Length: About 3 to 5 cm. Diameter: About 3 to 4 mm. Color: 191 B/C. Strength: Strong; flexible. Wing length: 2.5 to 4.5 cm. Wing diameter, base: About 1 to 2 mm. Wing color newer leaves, inner surface: 155A/B. Wing color newer leaves, outer surface: 155A/B. Wing color mature leaves ($4^{th}$ to $5^{th}$ leaf down from tip): 200B/C.

Root description: Fleshy, highly branched; 155D, typical of genus.

Inflorescence description: Inflorescence development has not been observed on plants of the new *Epipremnum.*

Disease resistance: Resistance to pathogens common to *Epipremnum* has not been observed on plants of the new *Epipremnum.*

COMPARISON WITH PARENTAL CULTIVAR

'UFM12' differs from plants of the parent, the cultivar 'Marble Queen', in the following characteristics:

1. 'UFM12' has leaves that are much smaller than the leaves of the parent plant.
2. 'UFM12' has leaves that are different in shape compared to leaves of the parent plant.
3. 'UFM12' has leaves that are not smooth compared with to the leaves of the parent plant.

We claim:

1. A new and distinct cultivar of *Epipremnum* plant named 'UFM12' as shown and described herein.

* * * * *